(12) United States Patent
Tal

(10) Patent No.: US 11,937,823 B2
(45) Date of Patent: Mar. 26, 2024

(54) GRADUALLY RESTRICTING VASCULAR BLOOD FLOW

(71) Applicant: VenaCore Inc., Wilmington, DE (US)

(72) Inventor: Michael Gabriel Tal, Tel Aviv (IL)

(73) Assignee: VenaCore Inc., Wilmington, DE (US)

( * ) Notice: Subject to any disclaimer, the term of this patent is extended or adjusted under 35 U.S.C. 154(b) by 92 days.

(21) Appl. No.: 17/625,657

(22) PCT Filed: Jul. 8, 2020

(86) PCT No.: PCT/US2020/041143
§ 371 (c)(1),
(2) Date: Jan. 7, 2022

(87) PCT Pub. No.: WO2021/007289
PCT Pub. Date: Jan. 14, 2021

(65) Prior Publication Data
US 2022/0296247 A1    Sep. 22, 2022

Related U.S. Application Data

(60) Provisional application No. 62/968,406, filed on Jan. 31, 2020, provisional application No. 62/872,085, filed on Jul. 9, 2019.

(51) Int. Cl.
*A61B 17/12* (2006.01)
*A61F 2/06* (2013.01)
*A61F 2/848* (2013.01)
*A61F 2/915* (2013.01)

(52) U.S. Cl.
CPC .. *A61B 17/12036* (2013.01); *A61B 17/12109* (2013.01); *A61B 17/12145* (2013.01);
(Continued)

(58) Field of Classification Search
CPC ............ A61B 17/1203; A61B 17/1204; A61B 17/12109; A61B 17/12145;
(Continued)

(56) References Cited

U.S. PATENT DOCUMENTS

| 5,383,926 A | 1/1995 | Lock et al. |
| 5,824,046 A | 10/1998 | Smith et al. |

(Continued)

FOREIGN PATENT DOCUMENTS

| DE | 60024592 T2 * | 7/2006 | ....... A61B 17/12118 |
| WO | 2009048367 A1 | 4/2009 | |

(Continued)

*Primary Examiner* — Erich G Herbermann
*Assistant Examiner* — Lindsey R. Rivers
(74) *Attorney, Agent, or Firm* — Veros Legal Solutions, LLP

(57) ABSTRACT

Disclosed are implant and method for gradually restricting vascular blood flow in a host blood vessel. The implant N comprising an elongated body and at least one holding member. Implant body comprising a flow restricting portion enclosing a variable minimal internal diameter. Holding member is configured for restraining implant body to maintain the variable minimal internal diameter in a first minimal internal diameter, and to physically yield voluntarily after a first predetermined average duration of being continuously subjected to internal human body conditions, thereby releasing and allowing the implant body to elastically deform voluntarily such that the variable minimal internal diameter changes to a second minimal internal diameter, smaller than the first minimal internal diameter.

15 Claims, 8 Drawing Sheets

(52) U.S. Cl.
CPC .............. *A61F 2/848* (2013.01); *A61F 2/915* (2013.01); *A61F 2002/068* (2013.01); *A61F 2230/005* (2013.01); *A61F 2250/0039* (2013.01)

(58) Field of Classification Search
CPC ........ A61B 17/12168; A61B 17/12172; A61B 17/12177; A61B 17/12027; A61F 2/848; A61F 2/915; A61F 2/06; A61F 2/82; A61F 2/01; A61F 2/0022; A61F 2002/068; A61F 2230/005; A61F 2250/0039; A61F 2250/001; A61F 6/146; A61F 6/22
See application file for complete search history.

(56) References Cited

U.S. PATENT DOCUMENTS

| | | |
|---|---|---|
| 5,954,765 A | 9/1999 | Ruiz |
| 6,336,937 B1 | 1/2002 | Vonesh et al. |
| 6,350,277 B1 | 2/2002 | Kocur |
| 6,878,160 B2 | 4/2005 | Gilligan et al. |
| 8,425,584 B2 | 4/2013 | Cully et al. |
| 2002/0045931 A1 | 4/2002 | Sogard et al. |
| 2003/0065386 A1 | 4/2003 | Weadock |
| 2004/0230288 A1 | 11/2004 | Rosenthal |
| 2006/0030920 A1 | 2/2006 | Ben-Muvhar |
| 2010/0010518 A1* | 1/2010 | Stopek ................... A61B 17/11 606/153 |
| 2013/0274648 A1 | 10/2013 | Weinberger |
| 2014/0121759 A1* | 5/2014 | Cully .................... A61L 31/022 623/1.18 |
| 2017/0042551 A1* | 2/2017 | Celermajer ............... A61F 2/06 |

FOREIGN PATENT DOCUMENTS

| | | |
|---|---|---|
| WO | 2019154802 A1 | 8/2019 |
| WO | 2019221971 A1 | 11/2019 |

* cited by examiner

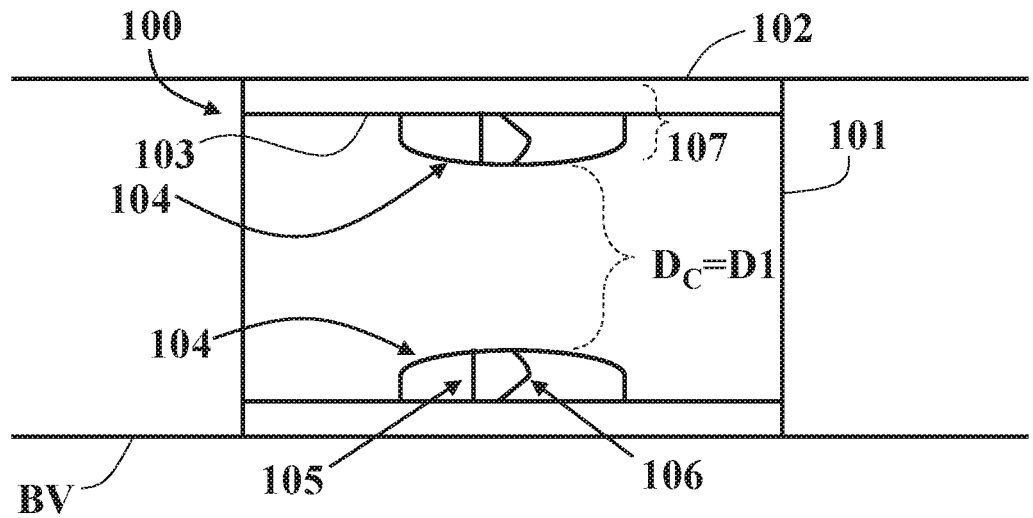
FIG. 3A (T=Ti)
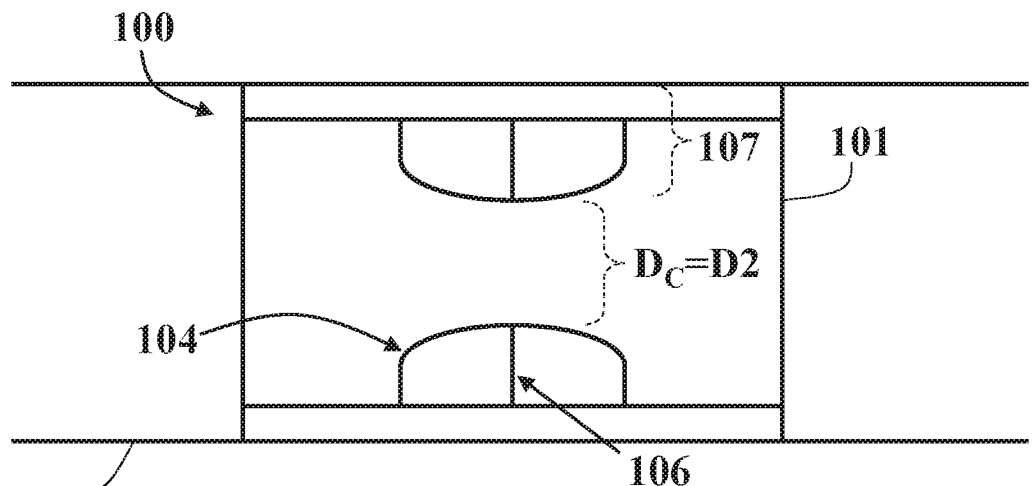
FIG. 3B (T=Ti+DT1)
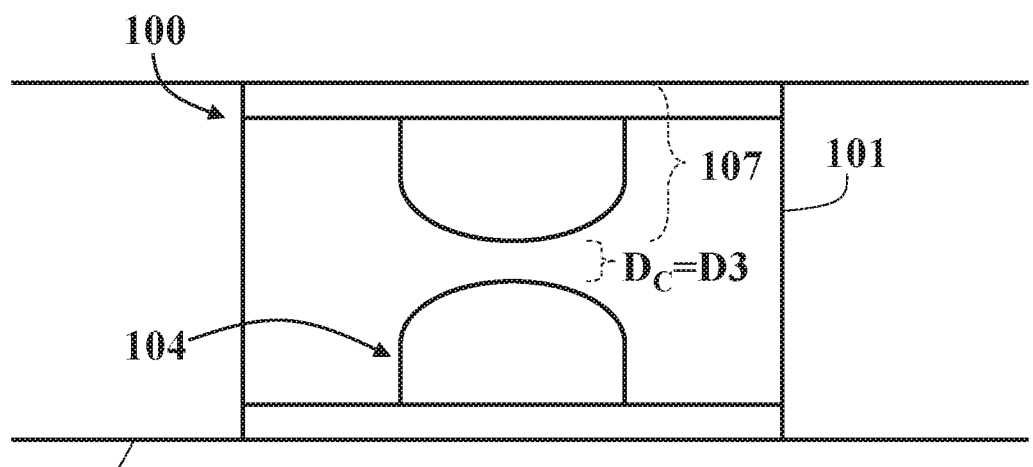
FIG. 3C (T=Ti+DT2)

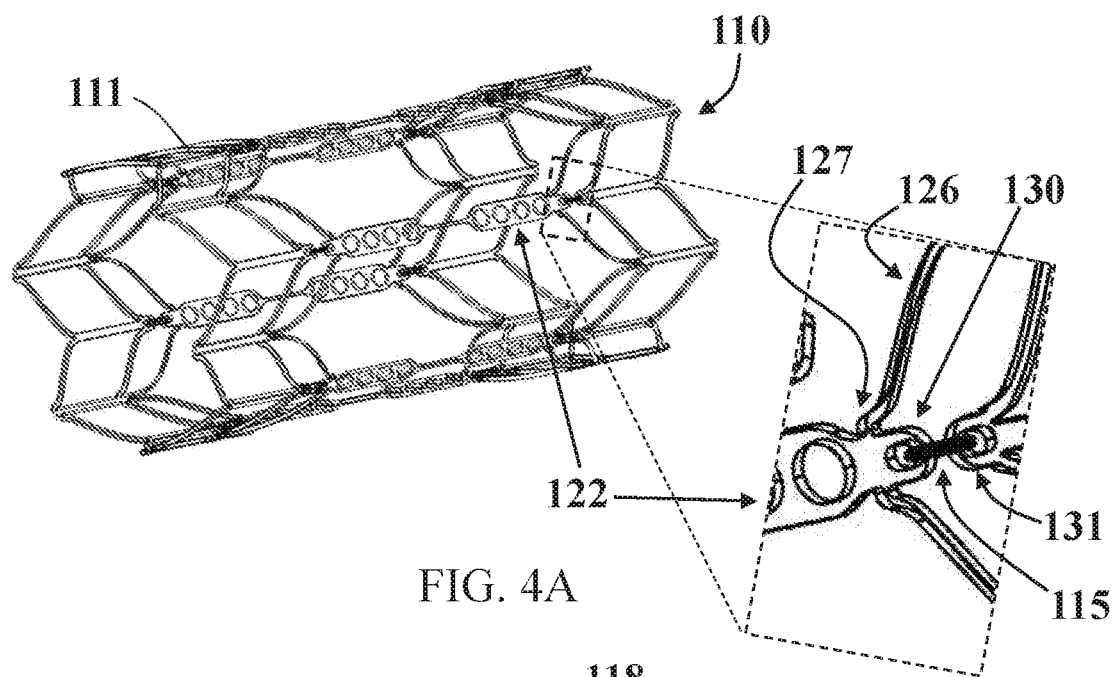
FIG. 4A
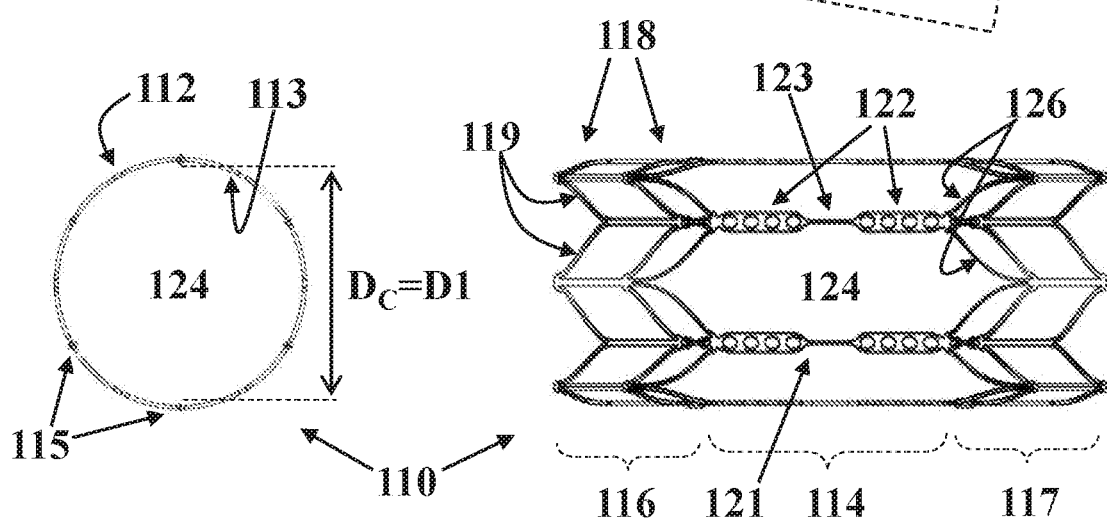
FIG. 4B
FIG. 4C
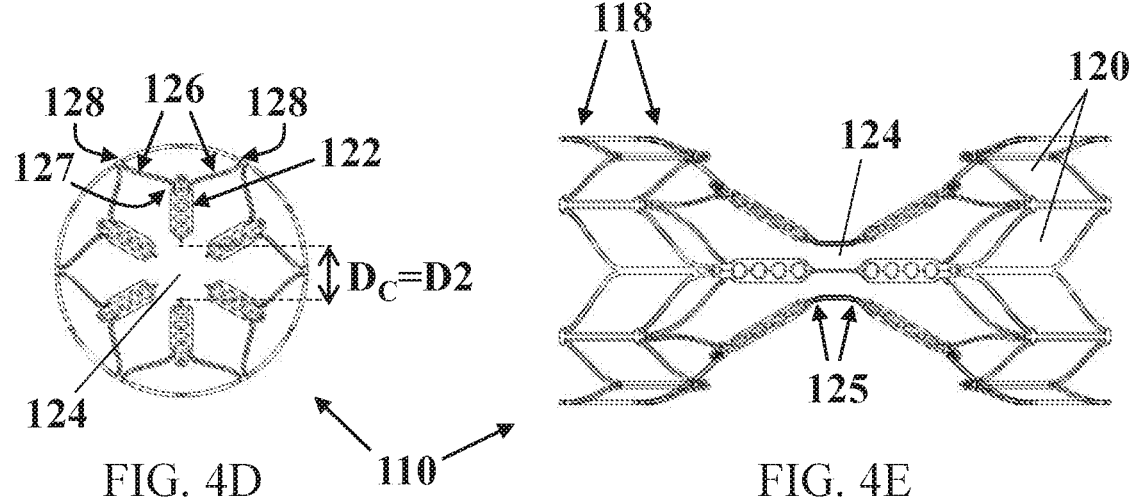
FIG. 4D
FIG. 4E

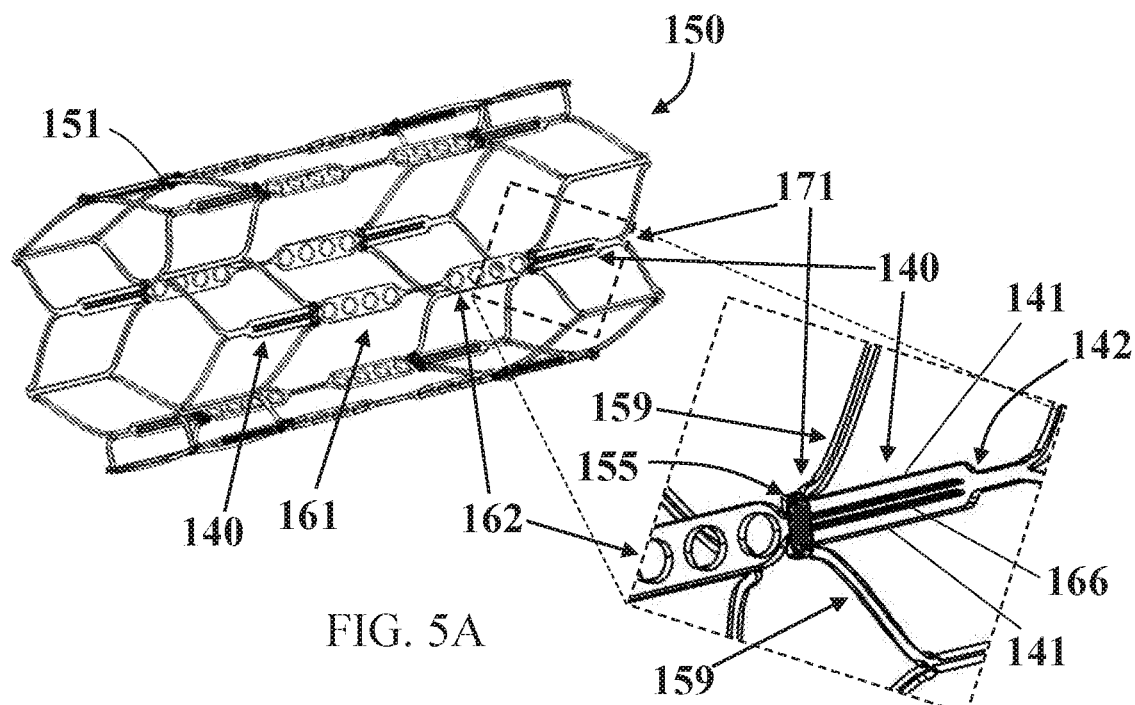

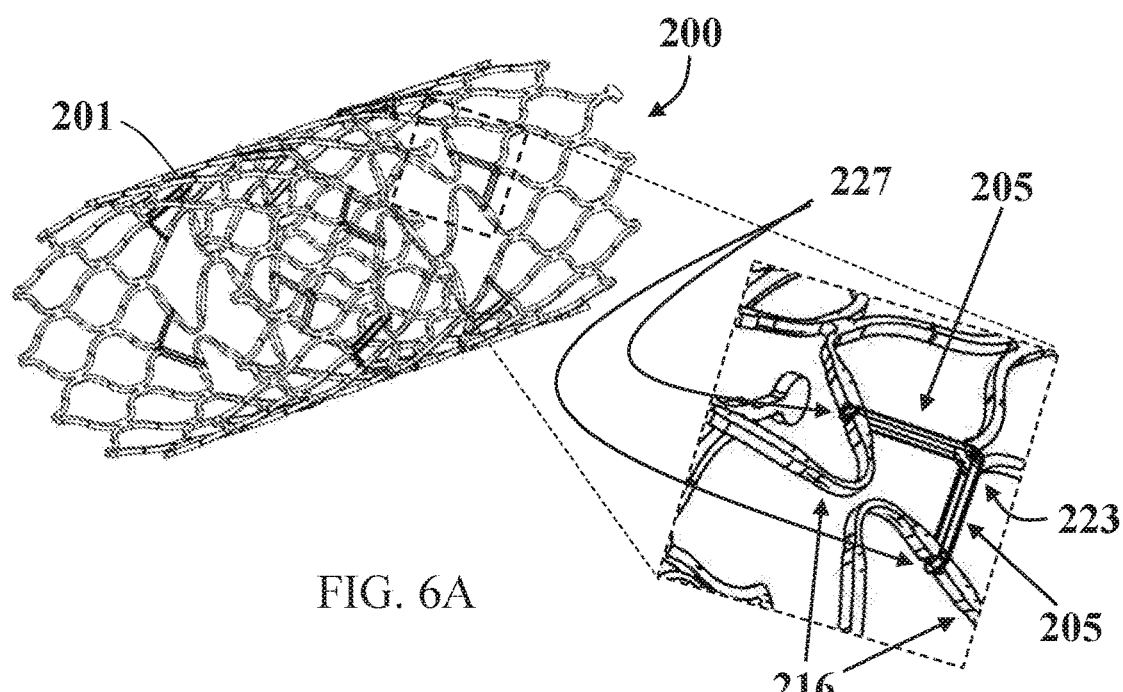
FIG. 6A
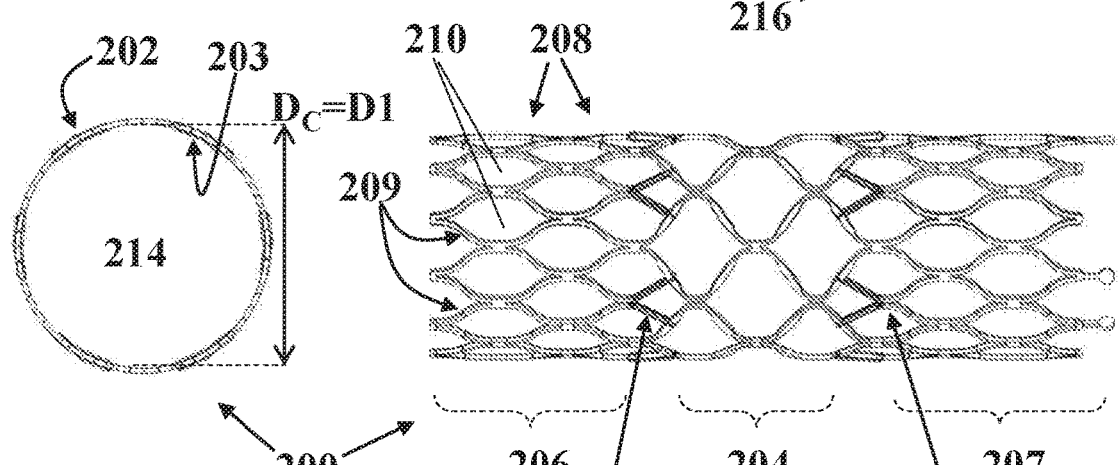
FIG. 6B
FIG. 6C
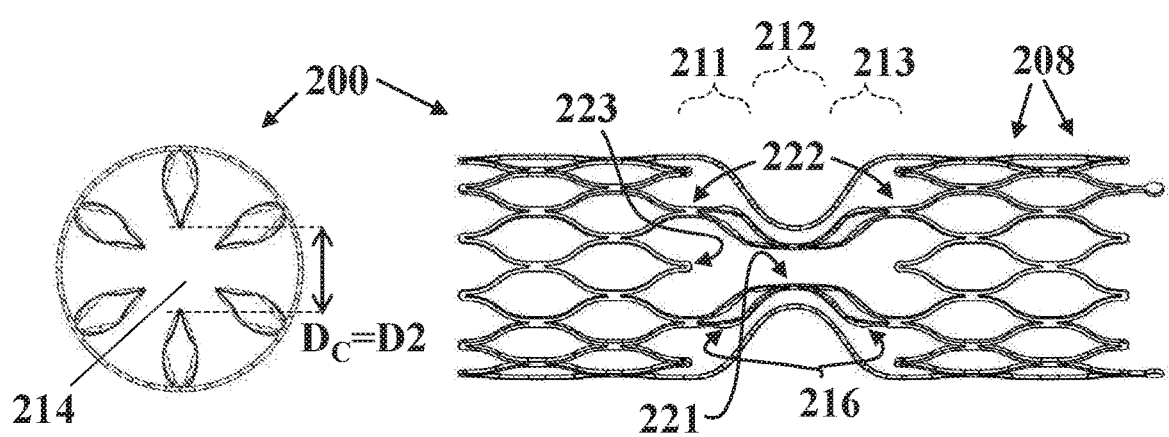
FIG. 6D
FIG. 6E

GRADUALLY RESTRICTING VASCULAR BLOOD FLOW

RELATED APPLICATIONS

This application claims priority to U.S. Provisional Application Ser. No. 62/872,085 filed Jul. 9, 2019, and U.S. Provisional Application Ser. No. 62/968,406 filed Jan. 31, 2020. The entire disclosures of all the related applications set forth in this section are hereby incorporated by reference in their entireties.

BACKGROUND

Congestive heart failure (CHF) occurs when the heart is unable to maintain required blood flow throughout body vasculature or parts thereof, due to reduced heart muscles contractibility or relaxation, commonly following traumatic or continuous change to heart structure and/or the function. Failure of the left side of the heart causes blood to congest in the lungs, causing respiratory symptoms as well as fatigue due to insufficient supply of oxygenated blood. Failure of the right side of the heart is often caused by pulmonary heart disease, which is usually caused by difficulties of the pulmonary circulation, such as pulmonary hypertension or pulmonic stenosis.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

The present disclosure relates to methods and devices for improving health and organs function by affecting flow in target bodily lumens, and more particularly, but not exclusively, to methods and devices for controlling blood flow rate in a blood vessel such as for treating or preventing health deterioration associated with congestive heart failure.

In certain embodiments, there is provided an implant for gradually restricting vascular blood flow. The implant can comprise:

an elongated implant body comprising a flow restricting portion enclosing a variable minimal internal diameter; and at least one first holding member configured for restraining the implant body to maintain the variable minimal internal diameter in a first minimal internal diameter, the at least one first holding member is configured to physically yield voluntarily after a first predetermined average duration of being continuously subjected to internal human body conditions, thereby releasing and allowing the implant body to elastically deform voluntarily such that the variable minimal internal diameter changes to a second minimal internal diameter, smaller than the first minimal internal diameter.

In some embodiments, at least a portion of the elongated body is configured as a stent and/or a mesh, and/or is formed by way of braiding, weaving, knitting, extruding or laser cutting.

In some embodiments, the first holding member is formed of a biodegradable material, optionally particularly configured as a biodegradable surgical suture.

In some embodiments, the implant further comprising at least one second holding member configured for restraining the implant body to maintain the variable minimal internal diameter in the second minimal internal diameter, after the first holding member physically yields, the second holding member is configured to physically yield voluntarily following a second predetermined average duration, greater than the first average duration, of being continuously subjected to human body conditions, thereby releasing and allowing the implant body to elastically deform voluntarily such that the variable minimal internal diameter changes to a third minimal internal diameter, smaller than the second minimal internal diameter.

In some embodiments, the first average duration is within a range of one day to one month, optionally particularly of one week to two weeks.

In some embodiments, the implant body includes a distal anchoring portion provided distally to the flow restricting portion and/or a proximal anchoring portion provided proximally to the flow restricting portion.

In some embodiments, the distal anchoring portion and/or the proximal anchoring portion are self-expandable or balloon-expandable for securing the implant body to an intralumenal surface of a host blood vessel.

In some embodiments, the distal anchoring portion and/or the proximal anchoring portion are expandable to a maximally allowed outer diameter being equal to or greater than an average lumen diameter of a superior vena cava in an adult human subject.

In some embodiments, the distal anchoring portion and/or the proximal anchoring portion are configured with a stent structure and includes a plurality of stent rings, each ring formed of a plurality of stent struts.

In some embodiments, the plurality of rings forms a plurality of stent cells therebetween.

In some embodiments, the flow restricting portion includes or is configured as one or more spaced-apart struts or cells collectively enclosing therebetween a constricted passage of the variable minimal internal diameter.

In some embodiments, the constricted passage is covered and/or impregnated with a flexible material configured to resist and/or block blood flow therethrough.

In some embodiments, the flow restricting portion is connected to the distal anchoring portion and/or the proximal retention portion via one or more elastic connecting members.

In some embodiments, each connecting member has elastically stressed portions when the variable minimal internal diameter is set in the first minimal internal diameter, the elastically stressed portions being configured to shift into a less elastically stressed state when the variable minimal internal diameter is set in the second minimal internal diameter.

In some embodiments, each connecting member is pulled towards the distal anchoring portion and/or the proximal anchoring portion by one or more of the at least one first holding member.

In some embodiments, each connecting member is fastened to the distal anchoring portion and/or the proximal anchoring portion by one or more of the at least one first holding member.

In some embodiments, each connecting member is forced into a straighten form by one or more of the at least one first holding member.

In some embodiments, the implant body includes a plurality of levers, each lever comprising a first lever end and a second lever end and is connected to the distal or proximal anchoring portion via a fulcrum portion provided between the first and second lever ends.

In some embodiments, the plurality of levers includes the flow restricting portion and collectively encloses the variable minimal internal diameter.

In some embodiments, the flow restriction portion is located between each of the respective fulcrum and second lever end.

In some embodiments, when the variable minimal internal diameter is set to the first minimal internal diameter, the at least one holding member engages the plurality of levers thereby generating a force at each first lever end configured to apply a continuous torque on the respective second lever end being sufficient to retain the respective second lever end in a first radial distance from a longitudinal axis of the elongated implant body.

In some embodiments, when the variable minimal internal diameter changes to a second minimal internal diameter, each one of the second lever ends shifts to a second radial distance from the longitudinal axis being smaller than the first radial distance.

In some embodiments, each one of the levers includes a lever body extending between the respective fulcrum portion and second lever end.

In some embodiments, the lever body is configured with a chosen elastic resistance to bending.

In some embodiments, the lever body is perforated and includes a series of holes along length thereof configured for allowing tissue ingrowth therein.

In some embodiments, the lever body includes sequential segments differentiated by resistance to flexing.

In some embodiments, the lever body has a distal segment ending adjacent to the second lever end, the distal segment is more compliant to flexing than other of the lever body segments and configured to at least partially conform to resistive forces applied by a wall portion of a host blood vessel fixated thereto when the variable minimal internal diameter changes to the second minimal internal diameter.

In some embodiments, the lever body has a proximal segment ending adjacent to the fulcrum portion, the proximal segment is more resistant to flexing than other of the lever body segments and configured to draw a wall portion of a host blood vessel fixated thereto when the variable minimal internal diameter changes to the second minimal internal diameter.

In some embodiments, at least one of the lever body segments includes weakening portions, optionally in a form of perforations, thru holes or blind holes.

In certain embodiments, there is provided a method for gradually restricting vascular blood flow in a host blood vessel. The method can comprise:

deploying an implant in the host blood vessel, the implant comprising an implant body and an at least one holding member, the implant body comprising a flow restricting portion enclosing a variable minimal internal diameter and the holding member is configured for restraining the implant body to maintain the variable minimal internal diameter in a first minimal internal diameter and to physically yield voluntarily after a first predetermined average duration of being continuously subjected to internal human body conditions;

allowing blood to flow in the host blood vessel through the flow restricting portion thereby continuously subjecting the holding member to the internal human body conditions for at least a period similar to the first predetermined average duration and after the holding member physically yields, thereby releasing and allowing the implant body to elastically deform voluntarily such that the variable minimal internal diameter changes to a second minimal internal diameter, smaller than the first minimal internal diameter, thereby restricting blood flowing through the flow restriction portion to a smaller flow rate or substantially blocking blood from flowing therethrough.

In some embodiments, the at least one holding member is formed of a biodegradable material, optionally particularly configured as a biodegradable surgical suture.

In some embodiments, the first average duration is within a range of one day to one month, optionally particularly of one week to two weeks.

In some embodiments, the implant body includes an at least one anchoring portion provided distally and/or proximally to the flow restricting portion, wherein the deploying includes affecting the at least one anchoring portion to expand until securing the implant body to the host blood vessel.

In some embodiments, the host blood vessel is a superior vena cava in an adult human subject.

In some embodiments, the first predetermined average duration is equal to or greater than duration sufficient for a normally occurring tissue growth on an artifact, originating from a wall portion of the host blood vessel, to surround and/or impregnate some or all surface of the implant body.

In some embodiments, following the first predetermined average duration and yielding of the at least one holding member the flow restricting portion is covered with tissue thereby enclosing a diameter equal to or smaller than the second minimal internal diameter.

All technical or/and scientific words, terms, or/and phrases, used herein have the same or similar meaning as commonly understood by one of ordinary skill in the art to which the invention pertains, unless otherwise specifically defined or stated herein. Illustrative embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments. In this regard, the description taken together with the accompanying drawings make apparent to those skilled in the art how some embodiments may be practiced.

FIGS. 3A-3C schematically illustrate different scenarios representing exemplary stages of a gradual voluntary change in constriction diameter affected by an exemplary implant, for gradually restricting vascular blood flow, according to some embodiments;

FIGS. 4A-4E illustrate views of a first exemplary implant before and after yielding of holding members thereof, according to some embodiments;

FIGS. 5A-5E illustrate views of a second exemplary implant before and after yielding of holding members thereof, according to some embodiments;

FIGS. 6A-6E illustrate views of a third exemplary implant before and after yielding of holding members thereof, according to some embodiments;

DETAILED DESCRIPTION

Certain embodiments relate to methods and devices for improving health and organs function by affecting flow in target bodily lumens, and more particularly, but not exclusively, to methods and devices for controlling blood flow rate in a blood vessel such as for treating or preventing health deterioration associated with congestive heart failure. In the event of severe constriction of the host blood vessel (e.g., the SVC), collateral pathways normally develop to increase blood transfer to tissues or organs. Although in some cases the pathways begin operating instantaneously upon constriction, a remodeling of the vessel is often required to allow the altered blood flow volumes. Since such remodeling may take up to several days to manifest, a gradual constriction over a period of one week or more may be advantageous to an abrupt constriction. A rapid severe constriction may result in stronger symptoms such as dyspnea, headaches, or swelling, for example.

Figure 1A:
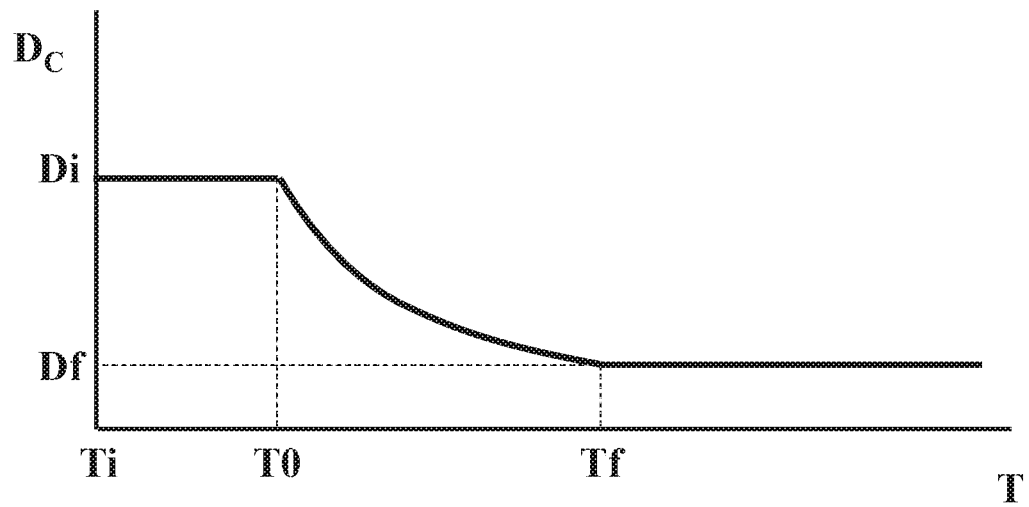
FIGS. 1A-1B illustrate exemplary graphs of gradual change in constriction diameter following implantation of exemplary implants in a blood vessel, according to some embodiments.
Figure 1B:
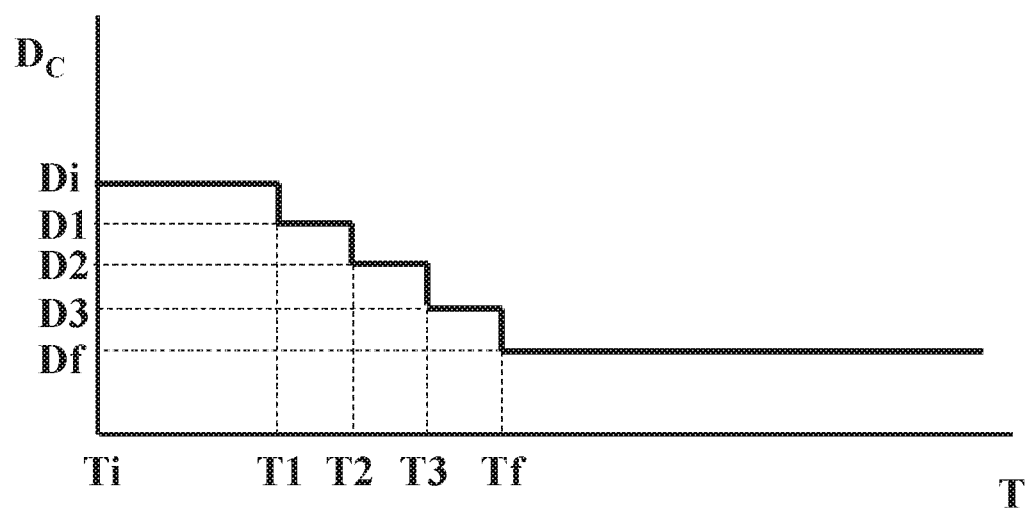

FIGS. 1A-1B illustrate exemplary graphs of gradual change in constriction diameter $D_C$ following implantation of exemplary implants in or externally over a host blood vessel. Implants, according to embodiments of the invention, are configured for prolonged (over weeks, months or years) or permanent implantation in/over a bodily lumen of a live subject, such as a blood vessel, optionally particularly a large blood vessel. In some embodiments, optionally linked to patients suffering from CHF, the host vessel is a large vein, optionally particularly a superior vena cava which returns deoxygenated blood from the systemic circulation directly to the right atrium of the heart. Constriction diameter $D_C$ will refer herein to minimal inner diameter affected by an exemplary implant, already implanted in/over a target blood vessel, through which most or all blood flowing in the target blood vessel is forced to pass by way of the implant structure.

Figure 2A:
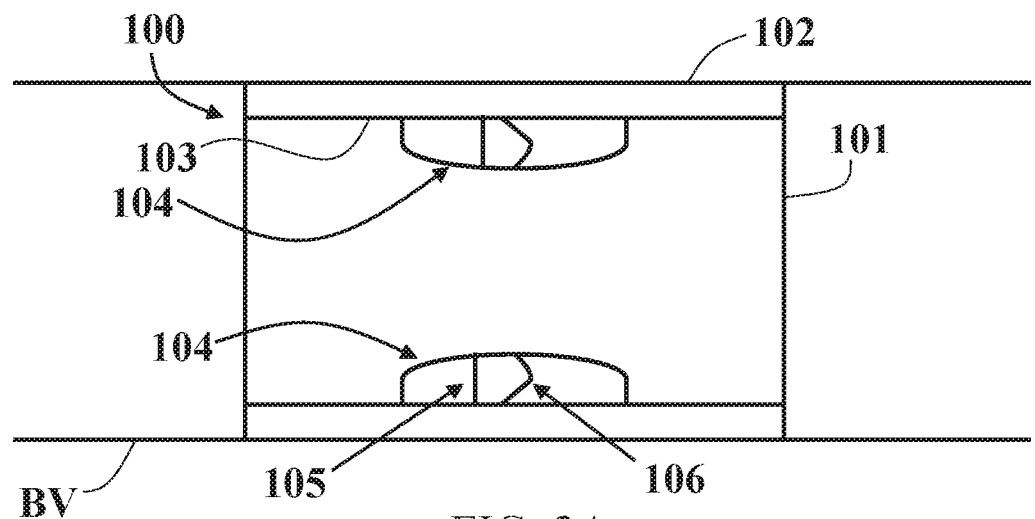
FIGS. 2A-2B schematically illustrate, respectively, exemplary intraluminal implant and extraluminal implant, configured for gradual voluntary constriction of a host blood vessel, according to some embodiments.
Figure 2B:
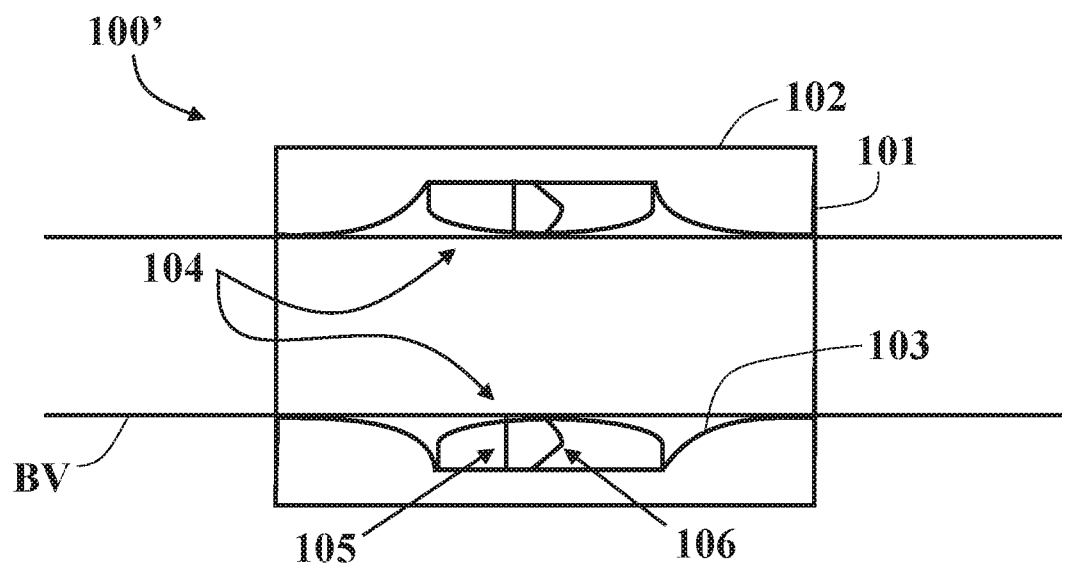

Exemplary implants include an elongated implant body having an outer tubular surface surrounding an inner tubular surface. In case of intraluminal implants (as shown in FIG. 2A, for example), their outer tubular surface is configured for interacting (e.g., anchoring and/or pressing against) with inner wall surface of the target blood vessel, and in case of extraluminal implants (as shown in FIG. 2B, for example), their outer tubular surface is configured for interacting (e.g., anchoring and/or pressing against) with outer wall surface of the target blood vessel. The inner tubular surface encloses a minimal internal diameter configured to gradually change (e.g., reduce) in size, voluntarily, until reaching to a final predetermined dimension.

FIG. 1A provides a schematic representation that demonstrates change in constriction diameter $D_C$ over time T, as affected by a first exemplary implant, wherein the first exemplary implant encloses an initial minimal inner diameter Di immediately upon implantation at implantation time Ti. The implant may be configured to immediately change in minimal inner diameter (i.e., constriction diameter $D_C$) however in this example it is configured to begin gradual reduction in minimal inner diameter at time T0, following a duration equal to T0-Ti. Duration T0-Ti is optionally predetermined or estimated based on a predetermined average duration. Initiation of reduction in diameter may be programmed or preset, structurally and/or functionally, in the implant so it can voluntarily initiate such change, or it can be initiated by an operator, optionally remotely to the implant. T0-Ti is optionally a few minutes or hours, or optionally a few days or weeks, such as between 2 days and 2 weeks. Optionally and alternatively, T0-Ti is negligible or zero.

Reduction in constriction diameter $D_C$ is gradual, optionally in a continuously reducing curve as shown, until reaching a predetermined final minimal inner diameter Df. Stopping diameter decrease at diameter Df can optionally be preset (i.e., set in advance to implantation), such as by providing a structural design of the implant that is restricted to final minimal inner diameter Df. The implant may also be configured to reach diameter Df upon reaching a final time Tf, following a duration equal to Tf-T0 or Tf-Ti. Duration Tf-T0 or Tf-Ti is optionally predetermined or estimated based on a predetermined average duration. Initiation of diameter reduction stop may be programmed or preset, structurally and/or functionally, in the implant so it can voluntarily initiate such stop in change, or it can be initiated by an operator, optionally remotely to the implant.

FIG. 1B provides a schematic representation that demonstrates change in constriction diameter $D_C$ over time T, as affected by a second exemplary implant, wherein the second exemplary implant encloses an initial minimal inner diameter Di immediately upon implantation at implantation time Ti. The implant is configured to maintain a certain minimal inner diameter (i.e., constriction diameter $D_C$) for a defined duration and then to reduce gradually, or relatively promptly (as shown), in minimal inner diameter into a smaller size. Such timely stepped reduction in diameter can be repeated in accordance with implant structural and/or functional design. In this example demonstrated in FIG. 1B, a first reduction in inner diameter from initial minimal inner diameter Di to a first minimal inner diameter D1 after a duration T1-Ti; then, a second reduction in inner diameter from first minimal inner diameter D1 to a second minimal inner diameter D2 after a duration T2-T1 or T2-Ti; then, a third reduction in inner diameter from second minimal inner diameter D2 to a third minimal inner diameter D3 after a duration T3-T2 or T3-Ti; then, a fourth reduction in inner diameter from third minimal inner diameter D3 to a final minimal inner diameter Df after a duration Tf-T3 or Tf-Ti. The implant can be design differently or configured to decrease or increase in number of stepped diameter reductions, and/or in each, or overall, stepped diameter reduction duration.

In some embodiments, Tf-Ti is less than a year, optionally equal to or less than 6 months, optionally equal to or less than 8 weeks, or optionally equal to or less than 4 weeks. In some embodiments, Df is 80% or less than Di, optionally 60% or less than Di, or optionally 30% or less than Di. In case of predetermined stepped reduction in constriction diameter $D_C$, D1 is optionally between 70% and 90% of Di and T1-Ti is between 1 week and 2 weeks, D2 is optionally between 50% and 80% of Di and T2-Ti is between 2 weeks and 4 weeks, D3 is optionally between 30% and 70% of Di and T2-Ti is between 3 weeks and 6 weeks. Initial minimal inner diameter Di is optionally between about 10 mm and about 40 mm, or optionally between about 14 mm and about 30 mm.

FIGS. 2A-2B schematically illustrate, respectively, exemplary intraluminal implant 100 and an equivalent extraluminal implant 100', each is configured for gradual voluntary constriction of a host blood vessel BV. FIGS. 3A-3C schematically illustrate different scenarios representing exemplary stages of a gradual voluntary change in constriction diameter $D_C$, as affected by implant 100, already implanted in a blood vessel BV, for gradually restricting vascular blood flow in blood vessel BV. Implant 100 or 100' is configured for prolonged or permanent implantation in/over the lumen of blood vessel BV and for restricting blood to flow mostly or only through a gradually reducing constriction diameter $D_C$ it defines. Implant 100/100' is structurally designed to change in minimal inner diameter thereby decreasing constriction diameter $D_C$ over time. Change in constriction diameter $D_C$ can be continuously linear (as shown in graph of FIG. 1A, for example), or have stepped reductions (as shown in FIG. 1B, for example), or any combination thereof.

Implant 100/100' includes an elongated implant body 101 having an outer tubular surface 102 surrounding an inner tubular surface 103. Elongated body 101 may be configured as a stent that can be formed by way of extruding or laser cutting, for example, and/or it can be configured as a mesh structure that can be formed by way of braiding, weaving or knitting, for example. Elongated body 101 can be self-expandable or is balloon-expandable to a maximally allowed outer diameter, for engaging with inner or outer wall surface of blood vessel BV. Such maximally allowed outer diameter is optionally equal to or greater than average lumen diameter of a superior vena cava in an adult human subject. Upon implantation, and as shown in FIG. 3A, implant body 101 has a first minimal internal diameter D1 enclosed by a portion 104 of inner tubular surface 103. Portion 104 may be part of a unitary structure forming implant body 101, or it may be part of an inner structure defining inner tubular surface 103 or part thereof, that is enclosed by an outer structure which defines outer tubular surface 102, for example.

In some embodiments, implant body 101 or inner part thereof is adapted to voluntarily (e.g., in response to internal elastic stresses) reduce constriction diameter $D_C$ from first minimal internal diameter D1 to final minimal internal diameter, which can be equal to or smaller than a third minimal internal diameter D3 shown in FIG. 3C. Reduction in constriction diameter $D_C$ is achievable by expanding a gap 107 formed between inner tubular surface 103 and outer tubular surface 102 while substantially maintaining outer diameter of implant body 101 formed by outer tubular surface 102.

For enabling gradual rather than immediate reduction in constriction diameter $D_C$, implant body 101 include structural members that alter structurally in time thereby affecting change to shape and/or size of implant 100/100'. Implant 100 or 100' may include a first holding member 105 configured for restraining implant body 101 to maintain portion 104 in first minimal internal diameter D1. First holding member 105 is configured to physically yield after a first predetermined average duration DT1, after being continuously subjected to human body conditions, thereby releasing inner tubular surface portion 104 and allowing implant body 101 to voluntarily thicken into having a second minimal internal diameter D2, smaller than first minimal internal diameter D1, as shown in FIG. 3B. Yielding in this context means that first holding member 105 or portion thereof undergo stresses that overcome their yield point such that they fail by either breaking, disintegrating, extending in size (e.g., elongating) maintained before yielding, or plastically deforming. Yielding may be gradual, such that first holding member 105 extends gradually hence constriction diameter $D_C$ reduces gradually until reaching second minimal internal diameter D2, or it can be immediate, such that first holding member 105 suddenly disintegrates hence constriction diameter $D_C$ promptly reaches second minimal internal diameter D2.

Implant 100/100' includes a second holding member 106 configured for restraining implant body 101 to maintain portion 104 in a second minimal internal diameter D2, after first holding member 105 has physically yielded. Second holding member 106 is configured to physically yield voluntarily after a second predetermined average duration DT2, greater than first average duration DT1, after being continuously subjected to human body conditions. Upon yielding of second minimal internal diameter D2, implant body 101 is released and allowed to voluntarily thicken into having a third minimal internal diameter D3, smaller than second minimal internal diameter D2, enclosed by inner tubular surface portion 104. First average duration DT1 is optionally between one day and one month, optionally particularly between one week and three weeks. Second average duration DT2 is at least a few days, at least 1 week or at least one month greater than first average duration DT1.

First holding member 105 and/or second holding member 106 can be formed of a biodegradable material, optionally particularly configured as a biodegradable surgical suture, meaning that their yielding point reduces in time until it become equal to or smaller than the overall stresses which eventually cause it to yield. In such embodiments, second holding member 106 is formed of different biodegradable material or blend, and/or different structure or dimensions, such that it fails substantially after first holding member 105 fails.

FIG. 3A shows implant 100 before first holding member 105 has yielded and second holding member 106 not fully stressed (e.g., fully extended in length). FIG. 3B shown implant 100 after first holding member 105 has yielded and failed, before or after it completely biodegraded, and second holding member 106 fully stressed and before it has yielded. FIG. 3C shows implant 100 after second holding member 106 has yielded and failed, before or after it completely biodegraded.

FIGS. 4A-4E illustrate views of an implant 110 configured for gradually restricting vascular blood flow. Implant 110 may be considered a first exemplary variation of intraluminal implant 100, intended for implantation site at a target location within a large blood vessel such as a super vena cava of an adult subject. Implant 110 includes an elongated implant body 111 having an outer tubular surface 112 surrounding an inner tubular surface 113. Inner tubular surface 113 includes a flow restricting portion 114 enclosing a variable minimal internal diameter Dc.

Flow restricting portion 114 includes a plurality of spaced-apart horizontal (i.e., generally parallel to the longitudinal axis of implant body 111) elongated members 121, collectively enclosing a constricted passage 124 of the variable minimal internal diameter Dc. Flow restricting portion 114 is optionally covered and/or impregnated with a flexible material, optionally formed of a stretchable and/or flexible polymer (e.g., PTFE sheath), which can resist or block blood flow therethrough such as in spaces formed in-between elongated members 121.

Each elongated member 121 includes widened and stiffer lateral portions 122 interconnected with a slender intermediate portion 123, so that each elongated member 121 can deform from a straighten form (shown in FIG. 4C, for example) to a collapsed form (shown in FIG. 4E, for example) when the intermediate portion 123 is pushed by the now-inclined lateral portions 122 to a radially-inwardly position. By shifting to the collapsed form, elongated members 121 collectively reduce variable minimal internal diameter Dc of constricted passage 124. Elongated members 121 are formed of elastic or super-elastic metal alloy (e.g., Ni—Ti or Co—Cr alloy), optionally by way of laser cutting, and configured with flexing portions 125 at both ends of intermediate portion 123 adjacent its adjoining to the respective lateral portion 122. Each flexing portion 125 is elastically stressed when variable minimal internal diameter Dc is set to first minimal internal diameter D1 (FIGS. 4B and 4C) and becomes less elastically stressed state when variable minimal internal diameter Dc is set to second minimal internal diameter D2 (FIGS. 4D and 4E).

Implant body 111 includes a distal anchoring portion 116 distally to flow restricting portion 114 and a proximal anchoring portion 117 proximally flow restricting portion 114, configured for allowing implant 110 delivery in the host blood vessel when provided in a narrower (e.g., collapsed) state. When implant 110 is positioned in a target location in the host blood vessel, distal anchoring portion 116 and proximal anchoring portion 117 can be expanded (together or sequentially) or allowed to expand up to a maximally allowed outer diameter being equal to or greater than the host blood vessel lumen. FIGS. 4A-4E show implant body 111 after expansion of both anchoring portions 116 and 117. Upon expansion, anchoring portions 116 and 117 fixate implant body 111 to the blood vessel by continuously pressing radially-outwardly with outer surface 112 (of anchoring portions 116 and 117) against inner wall of the host blood vessel, and optionally also locally support the blood wall from narrowing or collapsing, thereby holding flow restricting portion 114 in place.

The distal anchoring portion 116 and/or the proximal retention portion 117 may be either configured as a self-expandable structure (e.g., configured in a readily elastically deformable state) or as a balloon-expandable structure (e.g., configured in a readily plastically deformable state). Anchoring portions 116 and 117 are each configured with stent-like structure including a plurality of stent rings 118, each ring 118 is formed of a plurality of stent struts 119. The struts 119 are formed of elastic or super-elastic metal alloy (e.g., Ni—Ti or Co—Cr alloy) and shaped to facilitate controlled radial expansion. Rings 118 form a plurality of stent cells 120 therebetween to facilitate sufficient structural, longitudinal and radial strength.

Flow restricting portion 114 is connected to each one of distal anchoring portion 116 and proximal retention portion 117 with a pair elastic connecting members 126 formed like two slender legs. Each connecting member 126 in a pair is connected with one end 127 thereof at an opposite side of its respective lateral portion 122 of respective elongated member 121, adjacent free end 130 of lateral portion 122, and connected with other end 128 thereof to separate crest of inward ring 118. Each connecting member 126 has elastically stressed portions when variable minimal internal diameter Dc is set to first minimal internal diameter D1 (FIGS. 4B and 4C), which become less elastically stressed when variable minimal internal diameter Dc is set to second minimal internal diameter D2 (FIGS. 4D and 4E).

Implant 110 further includes an at least one holding member 115 configured for restraining implant body 111 to maintain variable minimal internal diameter Dc in a first minimal internal diameter D1. Holding member 115 is configured to maintain mechanical strength and integrity for keeping flow restricting portion 114 in a diameter equal or substantially close to first minimal internal diameter D1 for a chosen (e.g., predetermined) minimal, average or maximal duration, during which it is continuously subjected to internal human body conditions, and after such duration to physically yield voluntarily (without external interference), immediately or during a continuous progress, as a direct result of surrounding conditions affecting its mechanical properties. After holding members 115 yield, implant body 111 is released to elastically deform (voluntarily) such that variable minimal internal diameter Dc decreases from first minimal internal diameter D1 to a predetermined second minimal internal diameter D2. Holding member 115 is optionally formed of a biodegradable material, optionally configured as a biodegradable surgical suture, designed to dissolve and/or yield over a prescribed average time in a live subject body. The predetermined implantation duration until yield is optionally taken within a range of one day to one month, or from about one week to about two weeks.

Each elongated member 121 of flow restricting portion 114 is stretched into straightening by pulling in opposing directions from both free ends 130 of each elongated member 121 with a pair of oppositely positioned holding members 115. A single holding member 115 is wrapped through and between eyelets on free end 130 of each lateral portion 122 and on crest 131 of inward ring 118 closest to free end 130, and it extends in-between connecting members 126 of same elongated member 121. Holding member 115 is sized and configured to pull connecting members 126 towards distal anchoring portion 116 or proximal retention portion 117, forcing them to straighten and/or orient parallel to the longitudinal axis of implant body 111. After most or all holding members 115 yield, connecting members 126 are no longer forced to alignment and can deform a less elastically stressed form (shown in FIGS. 4D and 4E) in which they are inclined radially-inwardly to facilitate change of variable minimal internal diameter Dc to second minimal internal diameter D2. In some embodiments, some (e.g., about 50%) of holding members 115 are configured with substantially greater duration to yield in same bodily conditions, therefore causing a more gradual or stepped decline in minimal internal diameter Dc between first diameter D1 and second diameter D2.

FIGS. 5A-5E illustrate views of an implant 150 configured for gradually restricting vascular blood flow. Implant 150 may be considered a second exemplary variation of intraluminal implant 100, intended for implantation site at a target location within a large blood vessel such as a super vena cava of an adult subject. Implant 150 includes an elongated implant body 151 having an outer tubular surface 152 surrounding an inner tubular surface 153. Inner tubular surface 153 includes a flow restricting portion 154 enclosing a variable minimal internal diameter Dc.

Flow restricting portion 154 includes a plurality of spaced-apart horizontal (i.e., generally parallel to the longitudinal axis of implant body 151) elongated members 161, collectively enclosing a constricted passage 164 of the variable minimal internal diameter Dc. Flow restricting portion 154 is optionally covered and/or impregnated with a flexible material, optionally formed of a stretchable and/or flexible polymer (e.g., PTFE sheath), which can resist or block blood flow therethrough such as in spaces formed in-between elongated members 161.

Each elongated member 161 includes widened and stiffer lateral portions 162 interconnected with a slender intermediate portion 163, so that each elongated member 161 can deform from a straighten form (shown in FIG. 5C, for example) to a collapsed form (shown in FIG. 5E, for example) when the intermediate portion 163 is pushed by the now-inclined lateral portions 162 to a radially-inwardly position. By shifting to the collapsed form, elongated members 161 collectively reduce variable minimal internal diameter Dc of constricted passage 164. Elongated members 161 are formed of elastic or super-elastic metal alloy (e.g., Ni—Ti or Co—Cr alloy), optionally by way of laser cutting, and configured with flexing portions 165 at both ends of intermediate portion 163 adjacent its adjoining to the respective lateral portion 162. Each flexing portion 165 is elastically stressed when variable minimal internal diameter Dc is set to first minimal internal diameter D1 (FIGS. 5B and 5C) and becomes less elastically stressed state when variable minimal internal diameter Dc is set to second minimal internal diameter D2 (FIGS. 5D and 5E).

Implant body 151 includes a distal anchoring portion 156 distally to flow restricting portion 154 and a proximal anchoring portion 157 proximally flow restricting portion 154, configured for allowing implant 150 delivery in the host blood vessel when provided in a narrower (e.g., collapsed) state. When implant 150 is positioned in a target location in the host blood vessel, distal anchoring portion 156 and proximal anchoring portion 157 can be expanded (together or sequentially) or allowed to expand up to a maximally allowed outer diameter being equal to or greater than the host blood vessel lumen. FIGS. 5A-5E show implant body 151 after expansion of both anchoring portions 156 and 157. Upon expansion, anchoring portions 156 and 157 fixate implant body 151 to the blood vessel by continuously pressing radially-outwardly with outer surface 152 (of anchoring portions 156 and 157) against inner wall of the host blood vessel, and optionally also locally support the blood wall from narrowing or collapsing, thereby holding flow restricting portion 154 in place.

The distal anchoring portion 156 and/or the proximal retention portion 157 may be either configured as a self-expandable structure (e.g., configured in a readily elastically deformable state) or as a balloon-expandable structure (e.g., configured in a readily plastically deformable state). Anchoring portions 156 and 157 are each configured with stent-like structure including a plurality of stent rings 158, each ring 158 is formed of a plurality of stent struts 159. The struts 159 are formed of elastic or super-elastic metal alloy (e.g., Ni—Ti or Co—Cr alloy) and shaped to facilitate controlled radial expansion. Rings 158 form a plurality of stent cells 160 therebetween to facilitate sufficient structural, longitudinal and radial strength.

Flow restricting portion 154 is connected to each one of distal anchoring portion 156 and proximal retention portion 157 with an elastic connecting member 166 that extends throughout most or all its length between two legs 141 of a fork-like structure 140. Fork-like structure 140 is connected between two crests 171 in-between two struts 159 for closing two adjacent cells 160. Each connecting member 166 is connected with one end 167 thereof to end of lateral portion 162 and connected with other end 168 thereof to adjoining portion 142 of fork-like legs 141. Each connecting member 166 has elastically stressed portions when variable minimal internal diameter Dc is set to first minimal internal diameter D1 (FIGS. 5B and 5C), which become less elastically stressed when variable minimal internal diameter Dc is set to second minimal internal diameter D2 (FIGS. 5D and 5E).

Implant 150 further includes an at least one holding member 155 configured for restraining implant body 151 to maintain variable minimal internal diameter Dc in a first minimal internal diameter D1. Holding member 155 is configured to maintain mechanical strength and integrity for keeping flow restricting portion 154 in a diameter equal or substantially close to first minimal internal diameter D1 for a chosen (e.g., predetermined) minimal, average or maximal duration, during which it is continuously subjected to internal human body conditions, and after such duration to physically yield voluntarily (without external interference), immediately or during a continuous progress, as a direct result of surrounding conditions affecting its mechanical properties. After holding members 155 yield, implant body 151 is released to elastically deform (voluntarily) such that variable minimal internal diameter Dc decreases from first minimal internal diameter D1 to a predetermined second minimal internal diameter D2. Holding member 155 is optionally formed of a biodegradable material, optionally configured as a biodegradable surgical suture, designed to dissolve and/or yield over a prescribed average time in a live subject body. The predetermined implantation duration until yield is optionally taken within a range of one day to one month, or from about one week to about two weeks.

Each elongated member 161 of flow restricting portion 154 is stretched into straightening by pulling in opposing directions from both ends of each elongated member 161 with a pair of opposingly positioned holding members 155. A single holding member 155 is wrapped collectively around ends of fork-like legs 141 and base of connecting member 166 adjacent its adjoining portion with end of each lateral portion 162. Holding member 155 fastens connecting members 166 to distal anchoring portion 156 or proximal retention portion 157, forcing them to straighten and/or orient parallel to the longitudinal axis of implant body 151. After most or all holding members 155 yield, connecting members 166 are no longer forced to alignment and can deform a less elastically stressed form (shown in FIGS. 5D and 5E) in which they are inclined radially-inwardly to facilitate change of variable minimal internal diameter Dc to second minimal internal diameter D2. In some embodiments, some (e.g., about 50%) of holding members 155 are configured with substantially greater duration to yield in same bodily conditions, therefore causing a more gradual or stepped decline in minimal internal diameter Dc between first diameter D1 and second diameter D2.

FIGS. 6A-6E illustrate views of an implant 200 configured for gradually restricting vascular blood flow. Implant 200 may be considered a third exemplary variation of intraluminal implant 100, intended for implantation site at a target location within a large blood vessel such as a super vena cava of an adult subject. Implant 200 includes an elongated implant body 201 having an outer tubular surface 202 surrounding an inner tubular surface 203. Implant body 201 is configured as a stent-like structure comprising a plurality of stent rings 208, each ring 208 is formed of a plurality of stent struts 209. The struts 209 are formed of elastic or super-elastic metal alloy (e.g., Ni—Ti or Co—Cr alloy) and shaped to facilitate controlled radial expansion.

Rings 208 form a plurality of stent cells 210 therebetween to facilitate sufficient structural, longitudinal and radial strength.

Implant body 201 includes a flow restricting portion 204, a distal anchoring portion 206 distally to flow restricting portion 204 and a proximal anchoring portion 207 proximally flow restricting portion 204. Distal and proximal anchoring portions, 206 and 207, are similar or identical, including in terms of number, shape, pattern and design of its cells 210, whereas flow restricting portion 204 differs from distal and proximal anchoring portions by at least one its cell's design, shape, and orientation relative to the elongated axis of implant body 201 when in a relaxed (e.g., elastically not stressed) state, as shown in FIGS. 6D and 6E for example.

As shown in FIG. 6E, implant body 201 in the relaxed state is hourglass-like shaped with flow restricting portion 204 including a converging distal segment 211 connected to distal anchoring portion 206, then a neck segment 212 encompassing a portion of inner surface 203 enclosing a constricted passage 214 of a variable minimal internal diameter Dc, and a diverging proximal segment 213 connected to proximal anchoring portion 207. Flow restricting portion 204 is optionally covered and/or impregnated with a flexible material, optionally formed of a stretchable and/or flexible polymer (e.g., PTFE sheath), which can resist or block blood flow therethrough such as in spaces formed in-between cells 210 of flow restricting portion 204 (or constricted passage 214).

Distal and proximal anchoring portions, 206 and 207, are configured for allowing implant 200 delivery in the host blood vessel when provided in a narrower (e.g., collapsed) state. When implant 200 is positioned in a target location in the host blood vessel, distal anchoring portion 206 and proximal anchoring portion 207 can be expanded (together or sequentially) or allowed to expand up to a maximally allowed outer diameter being equal to or greater than the host blood vessel lumen. FIGS. 6A-6E show implant body 201 after expansion of both anchoring portions 206 and 207. Upon expansion, anchoring portions 206 and 207 fixate implant body 201 to the blood vessel by anchoring thereto (e.g., by continuously pressing radially-outwardly with outer surface 202 (of anchoring portions 206 and 207) against inner wall of the host blood vessel), optionally also locally supporting the blood wall from narrowing or collapsing, thereby holding flow restricting portion 204 in place. The distal anchoring portion 206 and/or the proximal retention portion 207 may be either configured as a self-expandable structure (e.g., configured in a readily elastically deformable state) or as a balloon-expandable structure (e.g., configured in a readily plastically deformable state).

Flow restricting portion 204 is connected to distal anchoring portion 206 and proximal retention portion 207 with elastic connecting members configured as restricting portion cells 216, each one is bent radially inwardly and encloses a narrow cell-opening when in relaxed state, as shown in FIG. 6E. Flow restricting portion 204 includes pairs of cells 216 peripherally spaced from each other around longitudinal axis of implant 200, each pair of cells 216 connects between distal anchoring portion 206 and proximal retention portion 207. Distal-most cells 216 collectively form distal segment 211 and each distal-most cell 216 is connected to a different connected peripheral crest 222 of distal anchoring portion 206. Likewise, proximal-most cells 216 collectively form proximal segment 213 and each proximal-most cell 216 is connected to a different connected peripheral crest 222 of proximal anchoring portion 207. Each pair of cells 216 has a connected portion 221 therebetween, all connected portions 221 collectively form neck segment 212. Each connected peripheral crest 222 is provided in-between adjacent unconnected peripheral crests 223 of distal anchoring portion 206 and proximal anchoring portion 207, respectively. Each restricting portion cell 216 has elastically stressed portions when variable minimal internal diameter Dc is set to first minimal internal diameter D1 (FIGS. 6B and 6C), which become less elastically stressed when variable minimal internal diameter Dc is set to second minimal internal diameter D2 (FIGS. 6D and 6E).

Implant 200 further includes a plurality of holding member 205 configured for restraining implant body 201 to maintain variable minimal internal diameter Dc in a first minimal internal diameter D1. Holding members 205 are configured to maintain mechanical strength and integrity for keeping flow restricting portion 204 in a diameter equal or substantially close to first minimal internal diameter D1 for a chosen (e.g., predetermined) minimal, average or maximal duration, during which it is continuously subjected to internal human body conditions, and after such duration to physically yield voluntarily (without external interference), immediately or during a continuous progress, as a direct result of surrounding conditions affecting its mechanical properties. After holding members 205 yield, implant body 201 is released to elastically deform (voluntarily) such that variable minimal internal diameter Dc decreases from first minimal internal diameter D1 to a predetermined second minimal internal diameter D2. Holding member 205 is optionally formed of a biodegradable material, optionally configured as a biodegradable surgical suture, designed to dissolve and/or yield over a prescribed average time in a live subject body. The predetermined implantation duration until yield is optionally taken within a range of one day to one month, or from about one week to about two weeks.

Flow restricting portion 204 is stretched with holding members 205 into straightened and radially expanded form by pulling in opposing directions from both ends thereof. Each one of unconnected peripheral crest 223 of distal anchoring portion 206 or of proximal anchoring portion 207 is tied to two mid-portions 227 of adjacent upper and lower connecting members 216, using one or more holding members 205. Holding members 205 are sized and configured to force restricting portion cells 216 to straighten and/or orient parallel to the longitudinal axis of implant body 201, thereby also expanding their cell-openings to a wider and shorter form relative to their narrow form when in the relaxed state. After one or more of holding members 205 yield, flow restricting portion 204 can voluntarily deform into a narrower form, such that the released connecting members 216 are no longer forced to alignment and can deform to a less elastically stressed form. After most or all holding members 205 yield, as shown in FIGS. 6D and 6E, connecting members 216 are inclined radially-inwardly to such that variable minimal internal diameter Dc changes to second minimal internal diameter D2. In some embodiments, some (e.g., about 50%) of holding members 205 are configured with substantially greater duration to yield in same bodily conditions, therefore causing a more gradual or stepped decline in minimal internal diameter Dc between first diameter D1 and second diameter D2.

Figure 7A:
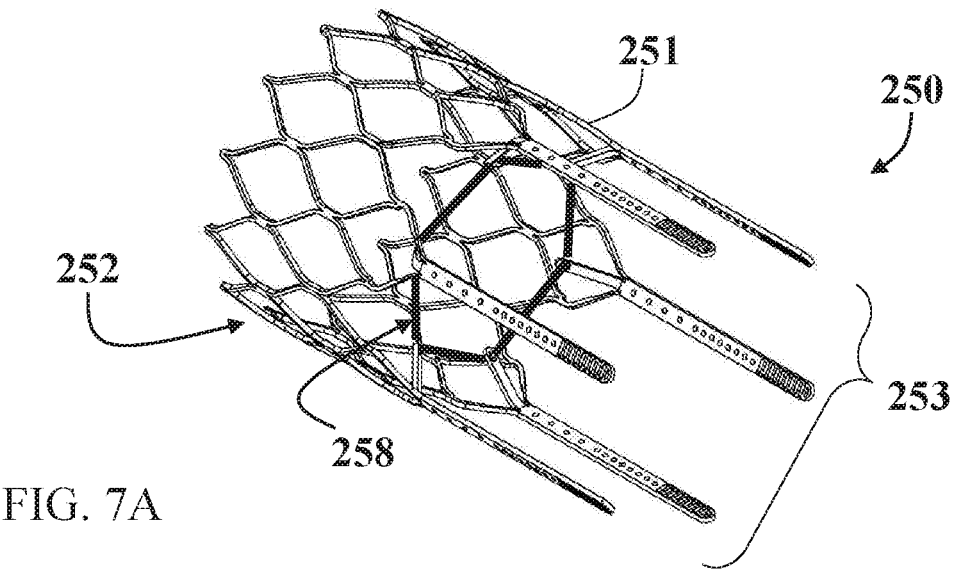
FIGS. 7A-7C illustrate views of a fourth exemplary implant before and after yielding of holding members thereof, according to some embodiments.
Figure 7B:
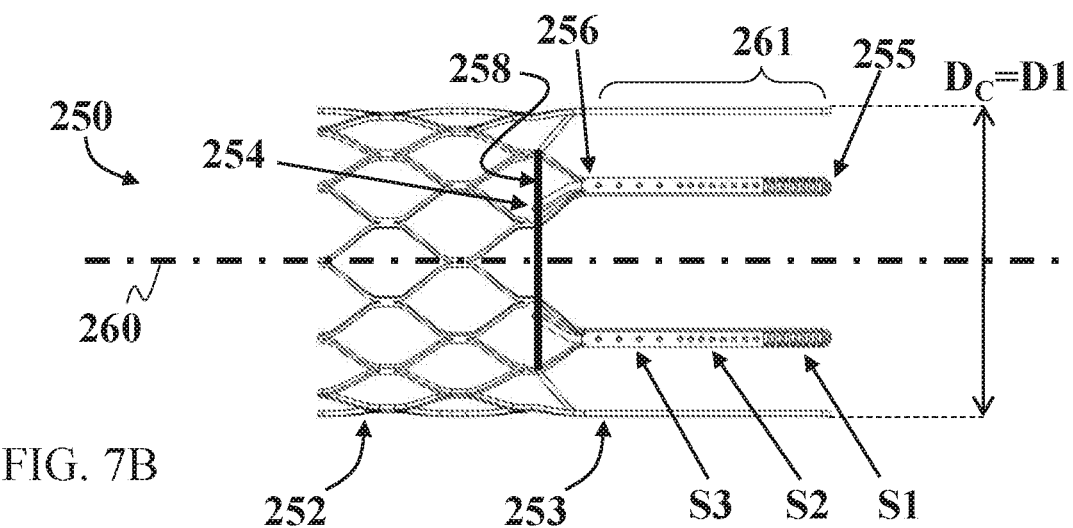
Figure 7C:
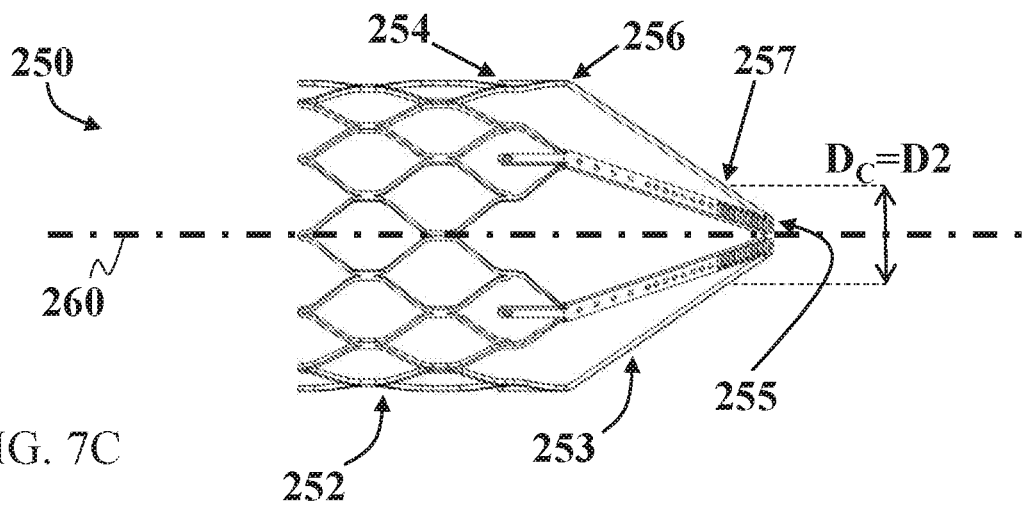

FIGS. 7A-7C illustrate views of an implant 250 configured for gradually restricting vascular blood flow and is shown before (FIGS. 7A and 7B) and after (FIG. 7C) yielding of holding members thereof when not being subjected to outside forces such as when implanted in a host blood vessel. Implant 250 may be considered a fourth exemplary variation of intraluminal implant 100, intended for implantation site at a target location within a large blood vessel such as a super vena cava of an adult subject. Implant 250 includes an elongated implant body 251 comprising an anchoring portion 252 provided distally or proximally to a plurality of levers 253 (in this example, a total of six levers 253). Each lever 253 comprising a first lever end 254 and a second lever end 255 and is connected to anchoring portion 252 via a fulcrum portion 256 provided between first and second lever ends 254 and 255. Levers 253 include a flow restricting portion 257 located between each of the respective fulcrum 256 and second lever end 255, and the levers collectively enclose a variable minimal internal diameter Dc with all flow restriction portions 257.

As shown in FIG. 7A, a holding member 258 in a form of a mailable or flexible tension member (e.g., configured as a wire or a suture) engages the plurality of levers 253 by passing through openings of all levers 253, that optionally distribute as a single opening per lever 253 located adjacent to each first lever end 254. Holding member 258 forms a closed loop sized and configured to generate (when tightened under sufficient tensioning force) a continuous inwardly directed pulling force at (and optionally equally divided between) each of the first lever ends 254, forcing each first lever end 254 to shift towards a longitudinal axis 260 of implant body 251. This pulling force applies a continuous torque (moment) on fulcrum portion 256 which is approximately equal to the product of the pulling force magnitude and distance between the first lever end 254 and fulcrum portion 256. This torque generates an outwardly directed pushing force at the respective second lever end 255 approximately equal to the quotient of the toque divided by the distance between second lever end 255 and fulcrum portion 256. The pushing forces shift second lever ends 255 radially outwardly away from longitudinal axis 260. The generated torque is configured as being sufficient to retain the respective second lever end 255 in a first radial distance from longitudinal axis 260. As such, holding member 258 restrains implant body 251 to maintain variable minimal internal diameter Dc in a first minimal internal diameter D1 as long as holding member 258 maintains it structural integrity and tension strength, and does not (at least not significantly) physically or mechanically yield or deform relative to its original state.

Each lever 253 includes a lever body 261 that extends between the respective fulcrum portion 256 and second lever end 255 and configured with a chosen elastic resistance to flexing (e.g., bending). Lever body 261 is perforated and includes a series of holes along length thereof configured for allowing tissue ingrowth therein. Lever body 261 includes sequential segments S1, S2 and S3 differentiated by their resistance to flexing, each segment includes weakening portions, optionally in a form of perforations, thru holes or blind holes, such that the quantity, size and/or density of the weakening portions in each segment causes the differentiation in resistance to flexing between the segments. In some embodiments, distal segment S1 of lever body 261 that ends adjacent to second lever end 255 is more compliant to flexing than the other segments S2 and S3 and is configured to at least partially conform to resistive forces applied by a wall portion of a host blood vessel fixated thereto when variable minimal internal diameter Dc changes to second minimal internal diameter D2. A proximal segment S3 that ends adjacent to fulcrum portion 256 is more resistant to flexing than the other segments S1 and S2 and is configured to draw a wall portion of a host blood vessel fixated thereto when variable minimal internal diameter Dc changes to second minimal internal diameter D2.

Holding member 258 is configured to physically yield voluntarily after a first predetermined average duration in which it is continuously subjected to internal human body conditions (e.g., average temperature between 35 and 39° C., for example). The first average duration is optionally within a range of one day to one month, optionally particularly of one week to two weeks, for allowing sufficient development of naturally occurring tissue growth for covering portions of implant 250, particularly portions of levers 253. In case levers 253 are perforated as shown, particularly along each lever body 261, this improves or facilitates increased fixation strength of the ingrowth tissue and host blood vessel wall to levers 253.

Yielding of holding member 258, optionally by breaking apart, disintegrating or plastically extending in length, for example, affects releasing and allowing implant body 251 to elastically deform voluntarily such that variable minimal internal diameter Dc changes to a second minimal internal diameter D2, smaller than the first minimal internal diameter D1. In some embodiments, holding member 258 is formed of a biodegradable material, optionally particularly configured as a biodegradable surgical suture. After yielding of holding member 258 and variable minimal internal diameter Dc changing to second minimal internal diameter D2, each one of the second lever ends 255 shifts to a second radial distance from longitudinal axis 260 being smaller than first radial distance thereto.

Anchoring portion 252 of elongated body 251 is optionally configured as a stent and/or a mesh, and/or is formed by way of braiding, weaving, knitting, extruding or laser cutting. In case that anchoring portion 252 is configured with a stent structure, it includes a plurality of stent rings, whereby each ring is formed of a plurality of stent struts. Anchoring portion 252 may be self-expandable or balloon-expandable for securing implant body 251 to an intralumenal surface of the host blood vessel, and is expandable to a maximally allowed outer diameter being equal to or greater than diameter of the host blood vessel lumen at the target implantation site, optionally greater than an average lumen diameter of a superior vena cava in an adult human subject.

Figure 8A:
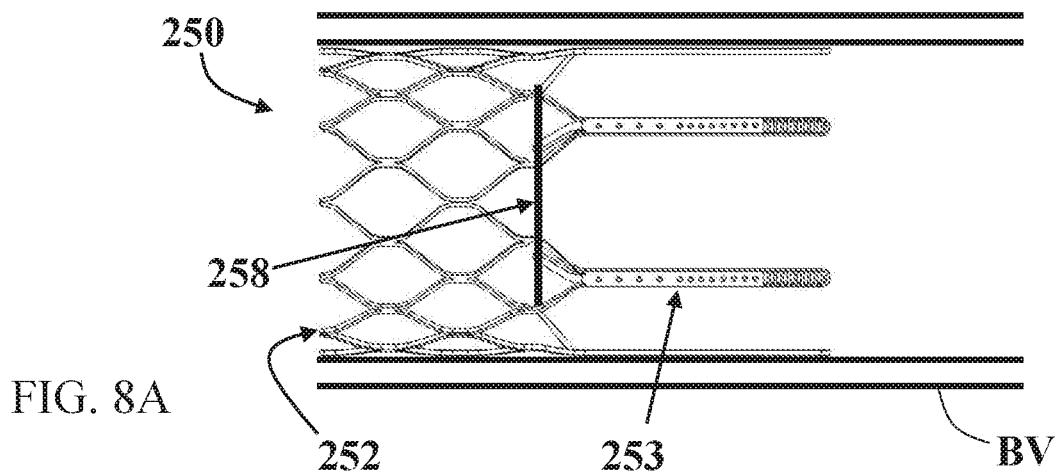
FIGS. 8A-8C schematically illustrate different scenarios representing exemplary stages in a method for gradually restricting vascular blood flow in a host blood vessel, according to some embodiments.
Figure 8B:
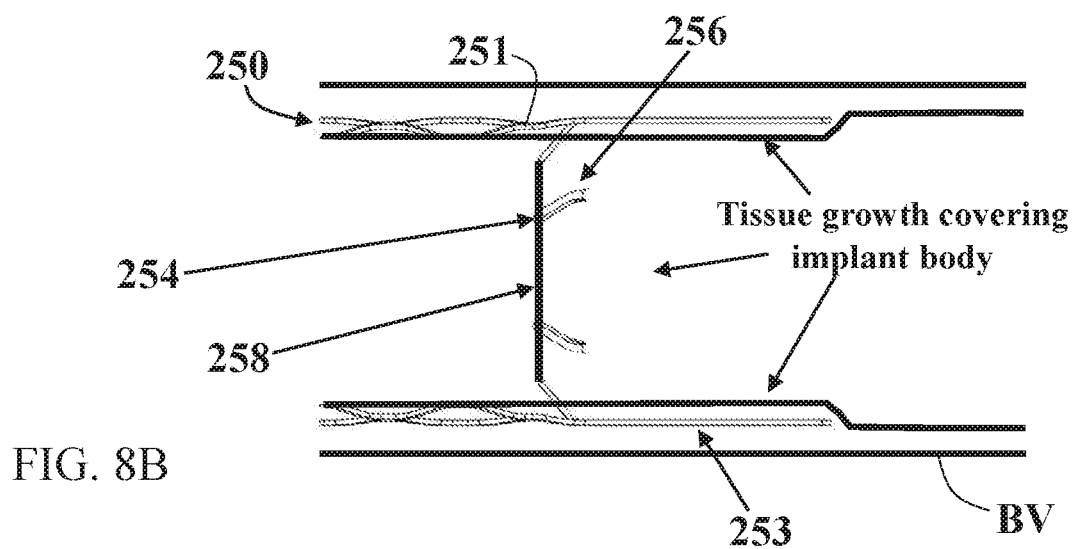
Figure 8C:
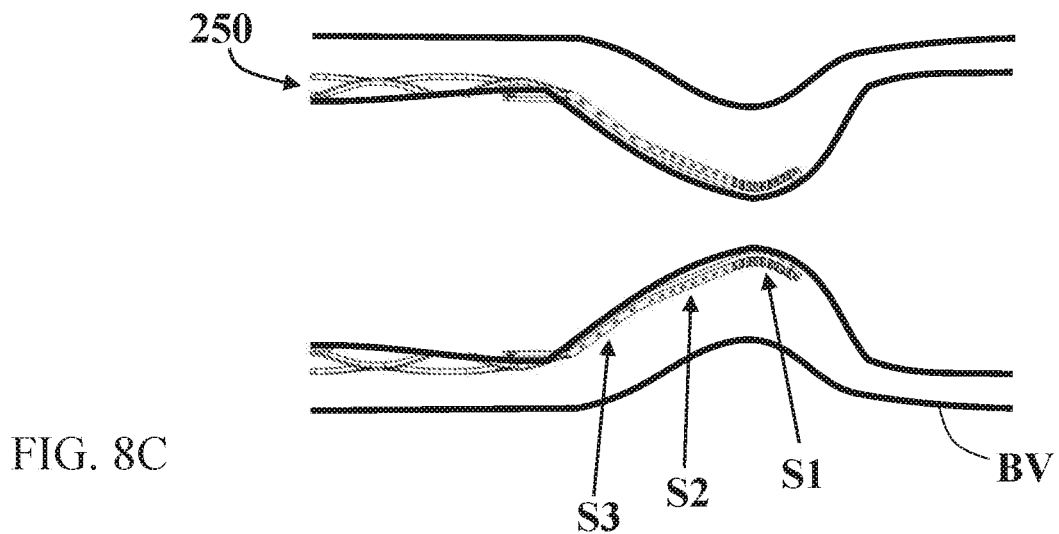

FIGS. 8A-8C schematically illustrate different scenarios representing exemplary stages in a method for gradually restricting vascular blood flow in a host blood vessel BV, optionally a superior vena cava in an adult human subject. FIG. 8A shows implant 250 immediately following deployment in the host blood vessel BV. As shown, anchoring portion 252 is expanded sufficiently to press radially outwardly against wall of host blood vessel BV thereby anchoring implant 250 thereto. Holding member 258 pulls first levers distal ends 254 of all levers 253 to approximate each other radially inwardly, such that lever body 261 of each lever 253 is shifted radially outwardly and approximate the blood vessel wall and optionally aligned substantially parallel thereto.

After deployment, blood can flow in host blood vessel BV through flow restricting portion 257, for at least a predetermined average duration within a range of one day to one month, optionally particularly of one week to two weeks. As such, the blood flow encounters only a minor interference that is possibly related to thickness and roughness of implant body 251 and/or to presence of holding member 258 in the way of the blood stream. In some embodiments, this average duration is predetermined according to known or estimated data to be equal to or greater than duration sufficient for a normally occurring tissue growth on an artifact, originating from a wall portion of the host blood vessel, to surround and/or impregnate some or all surface of implant body 251, wherein following the predetermined average duration the flow restricting portion 257 is covered with tissue thereby enclosing a diameter equal to or smaller than the second minimal internal diameter Dc, as shown in FIG. 8B.

After continuously subjecting holding member 258 to the internal human body conditions, for at least a period similar to the first predetermined average duration and after holding member 258 physically yields, implant body 251 is released to elastically deform voluntarily with the wall portion of host blood vessel BV covering it, such that the variable minimal internal diameter Dc changes to second minimal internal diameter D2, as shown in FIG. 8C. As such, blood is restricted to flowing through flow restriction portion 257 in a smaller flow rate or is substantially blocked from flowing therethrough.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. An implant for gradually restricting vascular blood flow, comprising:
    an elongated implant body comprising a flow restricting portion enclosing a variable minimal internal diameter;
    at least one first holding member configured for restraining the implant body to maintain the variable minimal internal diameter in a first minimal internal diameter, the at least one first holding member is configured to physically yield voluntarily after a first predetermined average duration of being continuously subjected to internal human body conditions, thereby releasing and allowing the implant body to elastically deform voluntarily such that the variable minimal internal diameter changes to a second minimal internal diameter, smaller than the first minimal internal diameter; and
    at least one second holding member configured for restraining the implant body to maintain the variable minimal internal diameter in the second minimal internal diameter, after the first holding member physically yields, the second holding member is configured to physically yield voluntarily following a second predetermined average duration, greater than the first average duration, of being continuously subjected to human body conditions, thereby releasing and allowing the implant body to elastically deform voluntarily such that the variable minimal internal diameter changes to a third minimal internal diameter, smaller than the second minimal internal diameter.

2. The implant according to claim 1, wherein at least a portion of the elongated body is configured as a stent and/or a mesh, and/or is formed by way of braiding, weaving, knitting, extruding or laser cutting.

3. The implant according to claim 1, wherein the first holding member is formed of a biodegradable material, optionally particularly configured as a biodegradable surgical suture.

4. The implant according to claim 1, wherein the first average duration is within a range of one day to one month, optionally particularly of one week to two weeks.

5. The implant according to claim 1, wherein the implant body includes a distal anchoring portion provided distally to the flow restricting portion and/or a proximal anchoring portion provided proximally to the flow restricting portion.

6. The implant according to claim 5, wherein the distal anchoring portion and/or the proximal anchoring portion are self-expandable or balloon-expandable for securing the implant body to an intralumenal surface of a host blood vessel.

7. The implant according to claim 5, wherein the distal anchoring portion and/or the proximal anchoring portion are expandable to a maximally allowed outer diameter being equal to or greater than an average lumen diameter of a superior vena cava in an adult human subject.

8. The implant according to claim 5, wherein the distal anchoring portion and/or the proximal anchoring portion are configured with a stent structure and includes a plurality of stent rings, each ring formed of a plurality of stent struts.

9. The implant according to claim 5, wherein the flow restricting portion includes or is configured as one or more spaced-apart struts or cells collectively enclosing therebetween a constricted passage of the variable minimal internal diameter.

10. The implant according to claim 9, wherein the constricted passage is covered and/or impregnated with a flexible material configured to resist and/or block blood flow therethrough.

11. An implant for gradually restricting vascular blood flow, comprising:
    an elongated implant body comprising a flow restricting portion enclosing a variable minimal internal diameter; and
    at least one first holding member configured for restraining the implant body to maintain the variable minimal internal diameter in a first minimal internal diameter, the at least one first holding member is configured to physically yield voluntarily after a first predetermined average duration of being continuously subjected to internal human body conditions, thereby releasing and allowing the implant body to elastically deform voluntarily such that the variable minimal internal diameter changes to a second minimal internal diameter, smaller than the first minimal internal diameter;
    wherein the implant body includes a distal anchoring portion provided distally to the flow restricting portion and/or a proximal anchoring portion provided proximally to the flow restricting portion, and wherein the flow restricting portion is connected to the distal anchoring portion and/or the proximal retention portion via one or more elastic connecting members.

12. The implant according to claim 11, wherein each connecting member has elastically stressed portions when the variable minimal internal diameter is set in the first minimal internal diameter, the elastically stressed portions being configured to shift into a less elastically stressed state when the variable minimal internal diameter is set in the second minimal internal diameter.

13. The implant according to claim 11, wherein each connecting member is pulled towards the distal anchoring portion and/or the proximal anchoring portion by one or more of the at least one first holding member.

14. The implant according to claim 11, wherein each connecting member is fastened to the distal anchoring portion and/or the proximal anchoring portion by one or more of the at least one first holding member.

15. The implant according to claim 11, wherein each connecting member is forced into a straightened form by one or more of the at least one first holding member.

* * * * *